(12) United States Patent
Felsenstein et al.

(10) Patent No.: US 12,042,222 B2
(45) Date of Patent: *Jul. 23, 2024

(54) LASER-ASSISTED TRANSDERMAL DELIVERY OF NANOPARTICULATES AND HYDROGELS

(71) Applicant: INTERNATIONAL BUSINESS MACHINES CORPORATION, Armonk, NY (US)

(72) Inventors: Jerome M. Felsenstein, Ossining, NY (US); James L. Hedrick, Pleasanton, CA (US); James J. Wynne, Mount Kisco, NY (US); Donna S. Zupanski-Nielsen, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 29 days.

This patent is subject to a terminal disclaimer.

(21) Appl. No.: 17/718,786

(22) Filed: Apr. 12, 2022

(65) Prior Publication Data
US 2022/0241012 A1     Aug. 4, 2022

Related U.S. Application Data

(60) Division of application No. 16/511,667, filed on Jul. 15, 2019, now Pat. No. 11,324,552, which is a
(Continued)

(51) Int. Cl.
*A61B 18/20* (2006.01)
*A61B 17/00* (2006.01)
(Continued)

(52) U.S. Cl.
CPC ............ *A61B 18/201* (2013.01); *A61B 18/20* (2013.01); *A61B 18/203* (2013.01);
(Continued)

(58) Field of Classification Search
None
See application file for complete search history.

(56) References Cited

U.S. PATENT DOCUMENTS 4,775,361 A    10/1988  Jacques et al.
4,784,135 A    11/1988  Blum et al.
(Continued)

FOREIGN PATENT DOCUMENTS

CN    102397621 A    4/2012

OTHER PUBLICATIONS

Allowance and Fees due in correspondence to U.S. Appl. No. 16/529,065 mailed on Nov. 9, 2022.
(Continued)

*Primary Examiner* — Carl H Layno
(74) *Attorney, Agent, or Firm* — Tutunjian & Bitetto, P.C.; Kristofer Haggerty

(57) ABSTRACT

A method for laser assisted delivery of therapeutic agents includes selectively controlling a valve connected to a first channel disposed within a first sidewall of a nozzle, applying, through the first channel, a first substance to penetrate dermis to a predetermined depth, and administering, through a second channel unconnected with the valve and disposed within a second sidewall of the nozzle, a second substance to remove debris.

19 Claims, 2 Drawing Sheets

Figure 1:
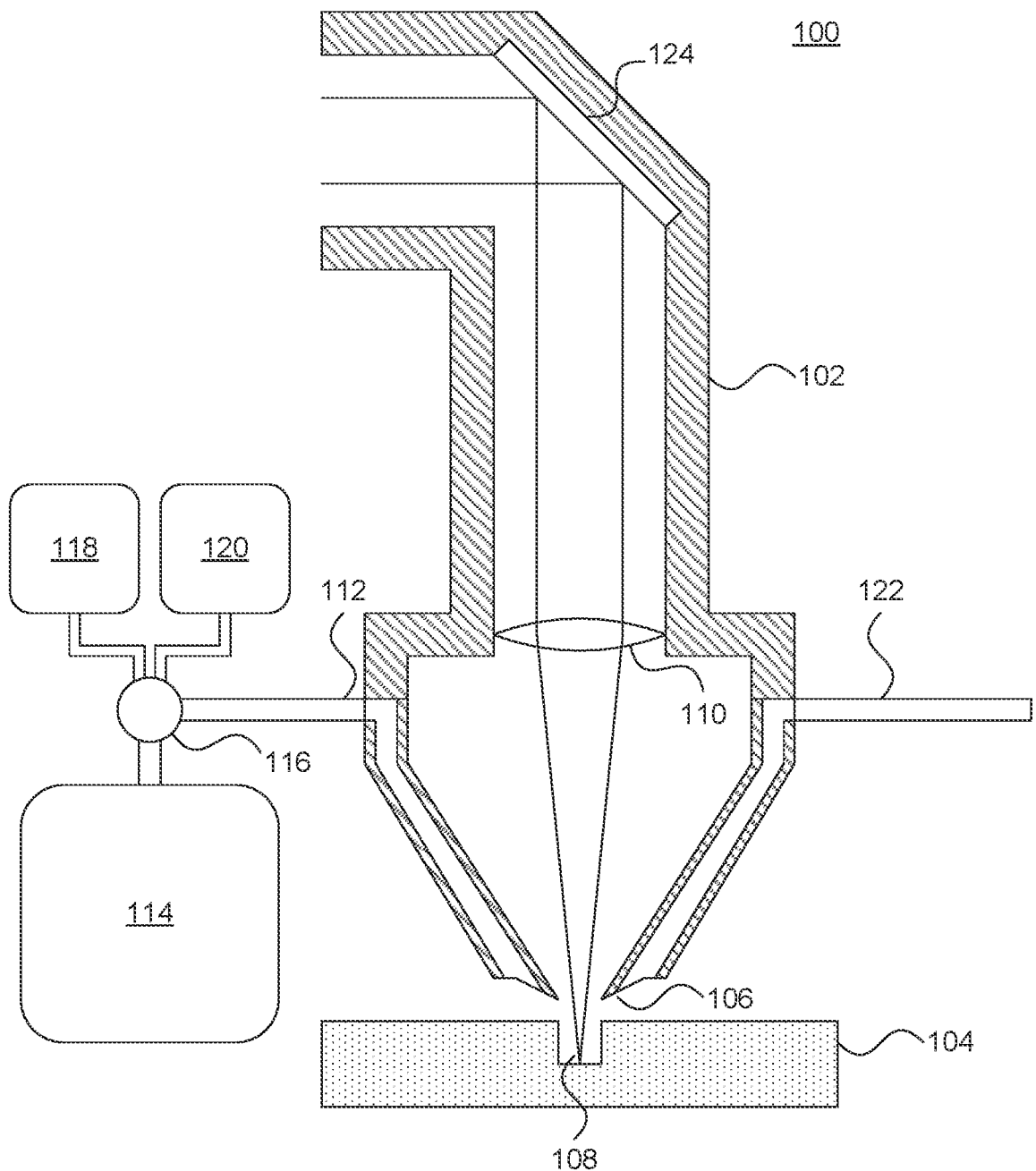

Related U.S. Application Data continuation of application No. 13/945,623, filed on Jul. 18, 2013, now Pat. No. 10,413,359.

(51) Int. Cl.

| | | |
|---|---|---|
| *A61B 18/00* | (2006.01) | |
| *A61B 90/00* | (2016.01) | |
| *A61K 9/00* | (2006.01) | |
| *A61M 37/00* | (2006.01) | |
| *A61N 5/06* | (2006.01) | |
| *A61N 5/067* | (2006.01) | |
| *A61Q 19/00* | (2006.01) | |

(52) U.S. Cl.
CPC ....... *A61K 9/0012* (2013.01); *A61M 37/0015* (2013.01); *A61N 5/0613* (2013.01); *A61Q 19/00* (2013.01); *A61B 2017/00765* (2013.01); *A61B 2018/0047* (2013.01); *A61B 2018/00577* (2013.01); *A61B 2018/20361* (2017.05); *A61B 2018/205547* (2017.05); *A61B 2090/062* (2016.02); *A61B 2090/3735* (2016.02); *A61M 2037/0007* (2013.01); *A61M 2037/0023* (2013.01); *A61M 2037/0061* (2013.01); *A61N 2005/0626* (2013.01); *A61N 2005/0627* (2013.01); *A61N 2005/0632* (2013.01); *A61N 2005/0661* (2013.01); *A61N 2005/0662* (2013.01); *A61N 5/067* (2021.08)

(56) References Cited

U.S. PATENT DOCUMENTS

| | | | |
|---|---|---|---|
| 4,904,340 | A | 2/1990 | Miracky et al. |
| 5,342,352 | A | 8/1994 | Franken et al. |
| 5,423,803 | A | 6/1995 | Tankovich et al. |
| 5,925,012 | A | 7/1999 | Murphy-Chutorian et al. |
| 5,980,512 | A * | 11/1999 | Silberg ................ A61B 18/203 606/9 |
| 6,056,738 | A | 5/2000 | Marchitto et al. |
| 6,162,211 | A | 12/2000 | Tankovich et al. |
| 6,165,170 | A | 12/2000 | Wynne et al. |
| 6,251,100 | B1 | 6/2001 | Flock et al. |
| 6,443,945 | B1 | 9/2002 | Marchitto et al. |
| 6,706,011 | B1 | 3/2004 | Murphy-Chutorian et al. |
| 6,902,562 | B1 | 6/2005 | Negus et al. |
| 8,134,098 | B2 | 3/2012 | Muratsubaki et al. |
| 8,263,900 | B2 | 9/2012 | Maehara et al. |
| 8,321,012 | B2 | 11/2012 | Della Rocca et al. |
| 8,753,332 | B2 | 6/2014 | Bragagna et al. |
| 8,961,501 | B2 | 2/2015 | Jarrett et al. |
| 9,987,427 | B1 | 6/2018 | Polsky et al. |
| 2002/0133147 | A1* | 9/2002 | Marchitto ............... A61B 5/411 606/9 |
| 2003/0100824 | A1* | 5/2003 | Warren ................ B33Y 30/00 600/407 |
| 2005/0059940 | A1* | 3/2005 | Weber ................. A61M 37/00 604/289 |
| 2006/0047329 | A1 | 3/2006 | Krespi et al. |
| 2007/0225779 | A1* | 9/2007 | Hantash ............. A61L 27/3804 424/1.17 |
| 2008/0103564 | A1* | 5/2008 | Burkinshaw ..... A61B 17/00491 604/181 |
| 2009/0093807 | A1 | 4/2009 | Hyde et al. |
| 2009/0131922 | A1 | 5/2009 | Dewey et al. |
| 2009/0287138 | A1 | 11/2009 | Latina |
| 2011/0130706 | A1* | 6/2011 | Kellogg ............. A61M 37/0015 604/20 |
| 2011/0130711 | A1* | 6/2011 | Lederman ............ A61B 18/203 606/167 |
| 2011/0130748 | A1* | 6/2011 | Kellogg ............... A61B 18/203 606/9 |
| 2012/0232542 | A1 | 9/2012 | Kasenbacher |
| 2013/0023966 | A1* | 1/2013 | Depfenhart .......... A61B 18/203 607/89 |
| 2013/0204238 | A1* | 8/2013 | Lederman ............... A61P 17/14 606/9 |
| 2014/0079686 | A1* | 3/2014 | Barman .................. A61K 8/69 424/94.67 |

OTHER PUBLICATIONS

List of IBM Patents or Patent Applications Treated as Related dated Apr. 11, 2022, 2 pages.

Office Action issued in corresponding U.S. Appl. No. 16/529,065, pp. 1-11.

AILU—The Association of Lawer Users. "Information Sheets—Cutting" www.ailu.org.uk. Copyrighted 2006-2013. (5 Pages) Available at: http://www.ailu.org.uk/laser_technology/information_sheets/process/information_sheet_-_cutting.html.

Andrews, S., et al. "Transdermal Delivery of Molecules is Limited by Full Epidermis, Not Just Stratum Corneum" Pharmaceutical Research. Nov. 2012. pp. 1099-1109.

Engler, A., et al. "Emerging trends in macromolecular antimicrobials to fight multi-drug-resistant infections" Nano Today, vol. 7, Issue 3. Jun. 2012. pp. 201-222.

Lee, A., et al. "The use of cholesterol-containing biodegradable block copolymers to exploit hydrophobic interactions for the delivery of anticancer drugs" Biomaterials, vol. 33, Issue 6. Feb. 2012. pp. 1921-1928.

Li, Y., et al. "Broad-Spectrum Antimicrobial and Biofilm-Disrupting Hydrogels:Stereocomplex-Driven Supramolecular Assemblies" Angewandte Chemie International Edition, vol. 51. Nov. 2012. pp. 1-6.

Liu, S., et al. "Antimicrobial and Antifouling Hydrogels Formed In Situ from Polycarbonate and Poly(ethylene glycol) via Michael Addition" Advanced Materials. Sep. 2012. pp. 1-6.

Nederberg, F., et al. "Biodegradable nanostructures with selective lysis of microbial membranes" Nature Chemistry, vol. 3. Apr. 2011. pp. 409-414.

Optotek Medical. "Products—Standard Articulated Arms" www.optotek-medical.com. Copyrighted 2009. (1 Page) Available at: http://www.optotek-medical.com/articulated-arms/standard-articulated-arms.

* cited by examiner

LASER-ASSISTED TRANSDERMAL DELIVERY OF NANOPARTICULATES AND HYDROGELS

CROSS-REFERENCE TO RELATED APPLICATIONS

This application is a Divisional application of U.S. Pat. No. 11,324,552 issued on May 10, 2022, which is a Continuation application of U.S. Pat. No. 10,413,359 issued on Sep. 17, 2019. This application is further related to U.S. Pat. No. 10,456,197 issued on Oct. 29, 2019, and U.S. Pat. No. 11,612,433 issued on Mar. 28, 2023.

BACKGROUND

Technical Field

The present invention relates to delivery of therapeutic and cosmetic substances and, more particularly, to laser-assisted delivery of a substance for a therapeutic or cosmetic purpose.

Description of the Related Art

Many disease states, such as cancer and infections, are treated by parenteral introduction of medication, radiation, or surgical excision with "cold steel" tools. These treatments all have negative side effects, for example, destruction of healthy tissue near the diseased tissue, systemic weakening of the immune system, increased susceptibility to other diseases and infections, production of scar tissue, and extended hospitalization time. Such treatments may also force the placement of a patient in a sterile environment, such as an operating room, with all of the associated costs.

Furthermore, in many cases of cosmetic modification, such as hair replacement, hair removal, introducing new collagen and interstitial matrix substances, and tattoo creation, there are high learning curves and practical difficulties in administering the treatments, each having its attendant side complications and undesirable side effects.

SUMMARY

A method for laser assisted delivery of agents includes preparing a site with an ultraviolet laser beam, at a wavelength appropriate for tissue ablation, such that an opening is produced in a surface of the site's tissue; and applying one or more agents to the prepared site, such that the agents penetrate the tissue through the opening to a predetermined depth.

Another method for laser assisted delivery of agents includes selectively controlling a valve connected to a first channel disposed within a first sidewall of a nozzle, applying, through the first channel, a first substance to penetrate dermis to a predetermined depth, and administering, through a second channel unconnected with the valve and disposed within a second sidewall of the nozzle, a second substance to remove debris.

Yet another method for laser assisted delivery of agents includes emitting a laser beam to form an opening in epidermis to expose dermis, selectively controlling a valve connected to a first channel disposed within a first sidewall of a nozzle, applying, through the first channel, a first substance to penetrate the dermis to a predetermined depth, and administering, through a second channel unconnected with the valve and disposed within a second sidewall of the nozzle, a second substance to remove debris.

Yet another method for laser assisted delivery of agents includes selectively controlling a valve connected to a first channel disposed within a first sidewall of a nozzle, applying, through the first channel, a first substance to penetrate dermis to a predetermined depth, verifying the application of the first substance to the predetermined depth with a non-invasive optical imaging technology, and administering, through a second channel unconnected with the valve and disposed within a second sidewall of the nozzle, a second substance to remove debris.

A laser treatment system includes an ultraviolet laser configured to produce a laser beam at a wavelength appropriate for tissue ablation; a lens configured to focus and direct the laser beam to a site, such that an opening is produced in a surface of the site's tissue; a nozzle having an aperture that emits the laser beam and that controls delivery of one or more agents to the site; and an imaging device configured to monitor a depth of penetration of the one or more agents into the site's tissue.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a cross-sectional view of a laser treatment system in accordance with the present principles;

FIG. 2 is a block/flow diagram of a method for laser-assisted treatment in accordance with the present principles; and FIG. 3 is a block diagram of a laser-treatment system in accordance with the present principles.

DETAILED DESCRIPTION OF PREFERRED EMBODIMENTS

Embodiments of the present invention provide therapeutic systems and methods that employ a laser to modify skin before introducing agents that can treat a variety of pathologic conditions and/or modify the skin cosmetically. This allows less invasive treatment, speeding healing and decreasing the likelihood and severity of side effects.

The targeting and controlled release of therapeutic agents to specific organs and specific cells in the body is one of the major challenges in developing more effective therapies. There are many materials challenges associated with the encapsulation, transport and release of such agents at a specific time and place in the complicated and dynamic environment of living organisms. The types of cargo can vary, but the majority of clinically used drugs are low molecular weight compounds that exhibit a short half-life in the blood stream and a high overall clearance rate. More recent advances in therapies include the use of proteins, peptides, DNA and siRNA that tend to succumb to proteases in the body, and hence need a delivery vehicle that can encapsulate and protect the fragile cargo during circulation. Currently, therapeutic cargos above molecular weights above 500 g/mol cannot penetrate the skin without the assistance of an external device, which often includes painful micro-needles or subcutaneous injections. The present embodiments are painless and have no therapeutic molecular weight or composition limitations as cargos of all sizes can be handled including high molecular weight therapeutics such as proteins and DNA. Moreover, the present embodiments allow a range of therapeutic delivery vehicles including nanoparticles, hydrogels and combinations thereof.

Referring now to the drawings in which like numerals represent the same or similar elements and initially to FIG. 1, a delivery arm 100 is shown. A laser beam 108 passes through housing 102 and is focused by lens 110 to a point on a working surface 104. In this case, the working surface 104 is the surface of a patient's skin. The laser beam 108 is, for example, a short pulse ultraviolet laser that locally removes the stratum corneum and, optionally, a controlled amount of epidermis, from the surface 104, to enable the delivery of agents through the modified skin to the desired sites. These agents are provided via a pipe 112 and are applied to the laser-modified surface 104 through nozzle 106.

One exemplary light source for the laser beam 108 is the argon fluoride excimer laser, which operates at a wavelength of about 193 nm in the vacuum ultraviolet (having a photon energy of about 6.4 eV). This wavelength is known to remove about one micrometer of tissue per pulse and provides a minimum of collateral damage. This is due to the fact that this wavelength is blocked by the aqueous chloride ion content of moist, viable tissue. The laser beam 108 may also include multiple wavelengths, for example including a relatively low-power visible wavelength. This provides visible illumination at the point of work, such that an operator can confirm that the laser is correctly aimed.

The laser beam 108 may be directed through the housing 102 by one or more mirrors 124. In an exemplary embodiment, a mirror 124 redirects the laser beam 108 at a 90-degree angle. The mirror 124 may also be controllable, such that the direction of the laser beam 108 may be set in two dimensions. The housing 102 may itself be adjustable through the use of one or more telescoping sections, allowing the length of the housing 102 to be adapted as needed.

The agents provided through nozzle 106 may include, e.g., cells, proteins, medications, and other chemicals. The agents are encapsulated within biodegradable hydrogels or nanoparticulates that are applied to the laser-modified surface 104 after laser irradiation. Such hydrogels may be polymeric and undergo biodegradation over a controllable time period, allowing for sustained release of the contained agents and treatment. The encapsulated agents may be stored in, e.g., a pressurized container 114, controlled by a valve 116, and may be ejected from a same cavity as the laser beam 108 itself. The lens 110 in this embodiment would be constructed to prevent encapsulated agents from traveling backward along the beam path.

The nanoparticulates stored in pressurized container 114 are dissolved and aggregated in water at a concentration that will ensure their kinetic stability in vivo once they are applied to the laser-modified skin surface 104. The hydrogels are soft, water-containing polymers, but are crosslinked to allow them to hold together. Hydrogels may be thought of as a dispersion of molecules of a liquid within a solid, where the solid is the continuous phase and the liquid is the discontinuous phase. Hydrogels are designed to have shear-lining capabilities. Under stress in a confined space, hydrogels flow. So the agent-containing nanoparticulates, hydrogels, and combinations thereof, may be stored in a pressurized container 114, to be ejected into the laser-created orifices in the skin when a valve 116 on pipe 112 is opened.

In addition to the therapeutic agent stored under pressure in container 114, the valve 116 may further control the application of a protective polymer 118 and a cleaning solution 120. The cleaning solution may be delivered through a pipe 112 to an annular dispensing nozzle 106 to clean/dissolve unwanted debris, with dry nitrogen gas delivered through a different pipe 122 to the nozzle 106 to evaporate the cleaning solution. The dry nitrogen gas may also be delivered to the chamber between the lens 110 and the tissue 108 to clear away debris that may result from the plume of material ablated from the skin 104 by the laser beam. The dry ditrogen gas flow may also serve to prevent backstreaming of material onto the lens.

Some exemplary therapeutic applications include localized chemotherapy, which eliminates the need for intravenous chemotherapy for skin cancers and thereby avoids the associated systemic side effects; destruction of fungus within, or underlying, a nail structure, where the laser could create small orifices through the nail, through which anti-fungal medication may be introduced; local destruction of cutaneous infections by introducing medication through laser-created channels directly into the diseased site; laser-assisted burn eschar debridement, followed by the application of hydrogels or nanoparticulates encapsulating skin stem cells to heal the debrided site; and treatment for necrotic fasciitis by laser debridement of necrotic tissue, followed by introducing hydrogels or nanoparticulates encapsulating anti-microbial and anti-toxin medication to the diseased sites.

Exemplary cosmetic applications may include stimulating hair growth by delivering stem cells from hair bulge and/or fat cells, as well as human dermal papillae, through laser-irradiated skin that is devoid of hair; skin rejuvenation by delivering autologous fibroblast stem cells into the laser-irradiated skin to produce new collagen matrix, acting as natural filler to alleviate wrinkles and grooves; safe introduction of tattoo dyes to specific, controlled depths without the attendant risk of infections and scarification, as well as the removal of such dyes; and facilitating permanent hair removal by introducing specific depilatory agents that arrest hair growth and/or destroy hair follicles with minimal side effects.

Some applications bridge the therapeutic and the cosmetic. Exemplary applications include delivering melanocytes or melanocyte-stimulating factors to vitiliginous skin to restore pigmentation and introducing sustained-release botox to axillae, palms of hands, and soles of feet to alleviate hyperhidrosis.

Specific applications for cancer treatments are possible following the present principles. A common feature of cancer is that cells lose their contact inhibition, where normal, non-cancerous cells stop growing when they make contact with adjacent cells. However, cancer cells may nonetheless have surface features that would allow the attachment of nanoparticulates or hydrogels, providing an opportunity to destroy or neutralize the cancer cells, while leaving normal cells undamaged.

Allergies, meanwhile, are normally treated by a series of injections with increased dosage of an allergen, which causes the body to build up a resistance. Such allergens can be delivered transdermally through laser-created orifices. The allergen can be contained within a biodegradable hydrogel that releases allergen in increasing and controlled amounts, until the hydrogel has completely degraded. Thus, a single treatment could replace an extensive series of injections.

Figure 2:
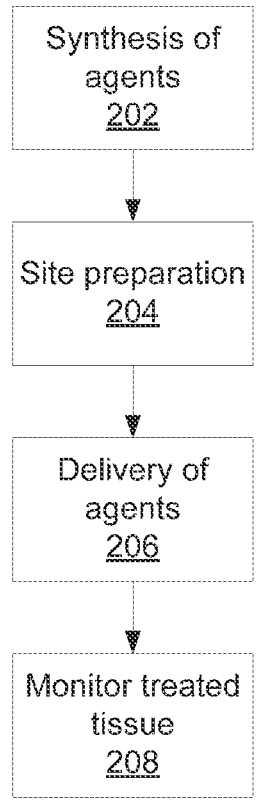

Referring now to FIG. 2, a diagram of a treatment method according to the present principles is shown. Block 202 prepares the agents to be used. In particular, this may include biodegradable/biocompatible polymeric nanoparticulates or hydrogels that are capable of the encapsulation of both hydrophobic and hydrophilic cargos into sub-150 nm particle sizes. The combination of small size and a hydrophilic, non-fouling outer layer of the particle allows long circulation time and accumulation into the diseased tissue through the enhanced permeation and retention effect (EPR) associated with the leaky vasculature around the tumor or infection. In addition, the molecular "tool box" allows the decoration of the nanoparticles with targeting ligands to further enhance the accumulation in the targeted site. These particles are designed to be hydrolytically stable, but degrade rapidly enzymatically into non-toxic starting materials that are easily cleared from the body.

Both covalent and non-covalent hydrogels may be used. These hydrogels have broad spectrum antimicrobial activity (Gram negative and positive) against yeast and fungi. These macromolecular drugs can be used alone or together with a traditional antibiotic to enhance the activity in a synergistic way. Hydrogels may have a nanostructure to encapsulate chemotherapeutics, proteins, siRNA and antibodies. The transdermal delivery of therapeutics from a degradable antimicrobial hydrogel over a 6 week period or so would preclude the need for weekly injections or painful subcutaneous injections.

In the case of cell implantation, a hydrogel may be used that adheres to the skin, feeds the growing cells, and reconfigures itself so as not to starve the cells over time. The adhesion may be based on natural adhesive proteins, such as those that mussels and barnacles use to adhere to rocks and boats.

For example, when treating cancerous tumors, efficient drug delivery needs novel nanocarriers that have a hydrophilic shell to prevent protein adsorption, thereby prolonging blood circulation, and a hydrophobic core for loading (typically hydrophobic or moderately polar) drugs. Nanosize agents allow passive targeting into tumor tissue based on an enhanced permeability and retention effect. Nanocarriers should possess one or more, and preferably all, of the following properties: 1) biodegradability and biocompatibility; 2) high loading capacity for various drugs; 3) kinetic stability after injection into the blood stream; 4) narrow size distribution for desirable and uniform biodistribution; and/or 5) biological ligands for active targeting to tumor tissues.

Polymer therapeutics may include polymeric micelles or nanoparticulates, to which drugs are covalently bound or physically incorporated. Alternatively, self-assembled block copolymer nanoparticulates may be several tens of nanometers in diameter with a relatively narrow size distribution and are a simple, economical, and versatile approach to nano-sized drug carriers. Bolstering the weak intermolecular interactions that effect nanoparticulate formation and stability may be accomplished by selectively crosslinking either the interior (core) or exterior (corona), crosslinking throughout the nanoparticulate, or stabilizing non-covalent interactions.

Despite the improved stability of chemical cross-linking, this approach may not be optimal in the encapsulation of a guest molecule or biodegradability. The precisely-tunable structure of block copolymers combined with new synthetic methodologies can allow the use of non-covalent interactions in polymeric assemblies. The role of non-covalent interactions is particularly pronounced as a collective driving force to the formation of stable aggregates as well as nanoparticulate-drug interactions.

Hydrogels can be made through physical or chemical crosslinking. Physically crosslinked hydrogels are formed by molecular entanglement and/or weak secondary forces such as Van der Waals interactions, ionic interactions, hydrogen bonding and hydrophobic interaction. A series of triblock copolymers have also been developed, which could be tuned to form hydrogels under physicological temperature via aggregation of percolated micelles. These hydrogels can sustain the release of the entrapped drugs, genes, and proteins and have potential applications in tissue engineering applications such as cartilage repair. Nonetheless, chemically crosslinked hydrogels are generally more robust than ones formed via ionic or physical interactions.

For the present embodiments, non-covalent hydrogels are advantageous as they shear thin, allowing ease of application similar to a lotion or a cream, even when loaded with therapeutic cargo. Moreover, such gels can be loaded with nanoparticulates and applied to the skin to mitigate the delivery rate of the loaded nanoparticulates. Those having ordinary skill in the art will recognize that there are many potential combinations of drug(s) and nanoparticulates embedded in a hydrogel for synergistic delivery.

Block 204 prepares the site. As described above, a laser beam 108 with fluence above the ablation threshold is directed to selected sites of cutaneous tissue 104, which will be irradiated by a pre-selected number of pulses to remove such tissue to a defined depth. The selected sites, which become entry points for the biodegradable nanoparticulates or hydrogels described in relation to block 202, could consist of one contiguous area or multiple non-continuous areas.

Because the cross section of the laser beam 108 at the irradiated skin surface 104 can be adjusted by changing the distance between the lens 110 and the surface 104, the orifices created in the skin surface 104 can be as small as about 200 nm and as large as several centimeters. Orifices larger than about 1 micrometer will allow the delivery of larger molecules, such as proteins, directly to the dermis layer of the skin.

Block 206 delivers the agents to the site. The pre-prepared nanoparticulates or hydrogels may be stored in a container, which can be pressurized to deliver a defined amount of such nanoparticulates or hydrogels to the laser-irradiated sites through an adjustable nozzle 106, which may deliver a narrow stream or a spray. Alternatively, the agents may be delivered to the skin as a cream that is spread over the skin's surface, filling the orifices.

Block 208 monitors the treated tissue using, for example, a non-invasive optical imaging method that images the treated tissue to verify the delivery of the nanoparticulates or hydrogels to the desired depth. An example of such a method is optical coherence tomography (OCT). OCT captures micrometer-resolution, three-dimensional images from within optical scattering media (e.g., biological tissue). OCT is an interferometric technique, typically employing near-infrared light. The use of relatively long wavelength light allows it to penetrate into the scattering medium. The nanoparticulate or hydrogel may be loaded with a non-toxic fluorescent dye, which fluoresces in the green or red region of the spectrum when illuminated by low power ultraviolet light or blue light. By imaging the three dimensional pattern of fluorescent light, the penetration of the nanoparticulate or hydrogel into the laser-created orifices in the skin is easily determined.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 3:
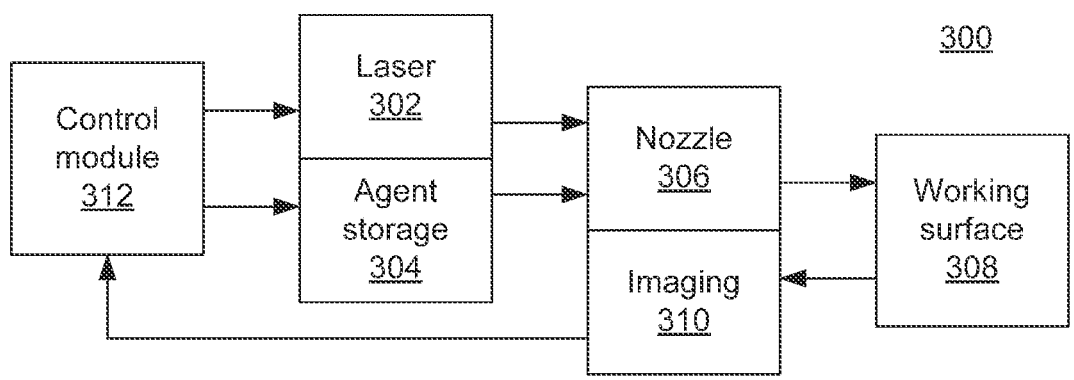

Referring now to FIG. 3, a block diagram of a laser delivery system 300 is shown. The laser 302, as noted above, may be an ArF excimer laser that generates a beam of ultraviolet light suitable for the ablation of tissue. The laser 302 generates pulses of this ultraviolet light, with each pulse removing a known amount of tissue at a desired diameter. Agent storage 304 holds the nanoparticulates and/or hydrogels that encapsulate the therapeutic or cosmetic agent to be applied. A control module 312 communicates with the laser 302 and the storage 304 and dictates when the laser 302 should emit a pulse and when the storage 304 should produce some of the agent.

As described above, the laser 302 and the agent storage 304 may be released from the same nozzle 306. This allows direct application of the agent to the treated site of the working surface 308 without moving the system. In most cases, the nozzle 306 will not need to be cleared in a separate process after application of the agent because the laser beam 108 itself will dissipate any of the agent that obstructs it.

An imaging module 310 monitors the working surface 308 as the agent is applied. The imaging module 310 determines a depth of penetration of the agents and communicates this information to the control module 312. Based on the depth of penetration, the control module 312 determines whether to provide additional agent to the working surface 308. When sufficient penetration is achieved, the nozzle 306 may be moved to the next treatment site on the working surface 308.

Having described preferred embodiments of a system and method for laser-assisted transdermal delivery of nanoparticulates and hydrogels (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method comprising:
    emitting an ultraviolet laser beam toward skin from a nozzle of a laser device, the nozzle extending from a housing that contains a lens positioned to direct the ultraviolet laser beam to a working surface at an end of the nozzle;
    forming an opening in an epidermis of the skin and exposing a dermis of the skin with the laser beam at the working surface;
    selectively controlling a valve connecting a plurality of reservoirs to a first channel disposed within a first sidewall of the nozzle, the valve controlling which of the plurality of reservoirs is in communication with the first channel, the first sidewall extends from the working surface to the housing that contains the lens, and the first channel having an opening to the working surface at the end of the nozzle;
    selectively administering a first substance from one of the plurality of reservoirs, through the first channel, and penetrating the dermis to a predetermined depth with the first substance; and
    verifying a presence of the first substance to the predetermined depth with a non-invasive optical imaging technology.

2. The method of claim 1, further comprising administering a second substance, through a second channel unconnected with the valve and disposed within a second sidewall of the nozzle and removing debris with the second substance.

3. The method of claim 1, wherein the first substance includes a therapeutic of cosmetic substance.

4. The method of claim 1, wherein the first substance is encapsulated in a biodegradable sheath.

5. The method of claim 1, wherein the ultraviolet laser beam has at least one wavelength in an ultraviolet spectrum to provide epidermis ablation.

6. The method of claim 1, wherein administering the first substance includes spraying the first substance from a same aperture that emits the ultraviolet laser beam.

7. The method of claim 1, wherein the first substance includes nanoparticles.

8. The method of claim 1, wherein the first substance includes hydrogels.

9. The method of claim 8, wherein the hydrogels are polymeric and undergo biodegradation over a controllable time period.

10. The method of claim 7, wherein the hydrogels are water-containing polymers that are crosslinked.

11. The method of claim 8, wherein the hydrogels are covalent hydrogels.

12. The method of claim 8, wherein the hydrogels are non-covalent hydrogels.

13. The method of claim 1, wherein the non-invasive optical imaging technology includes optical coherence tomography (OCT).

14. The method of claim 1, wherein the non-invasive optical imaging technology includes fluorescence imaging.

15. A method comprising:
    emitting an ultraviolet laser beam toward skin from a nozzle of a laser device, the nozzle extending from a housing that contains a lens positioned to direct the ultraviolet laser beam to a working surface at an end of the nozzle;
    forming an opening in an epidermis of the skin and exposing a dermis of the skin with the laser beam at the working surface;
    selectively controlling a valve connecting a plurality of reservoirs to a first channel disposed within a first sidewall of the nozzle, the valve controlling which of the plurality of reservoirs is in communication with the first channel, the first sidewall extends from the working surface to the housing that contains the lens, and the first channel having an opening at the working surface at the end of the nozzle,
    selectively administering hydrogels from one of the plurality of reservoirs, through the first channel, and penetrating the dermis to a predetermined depth with the hydrogels; and
    verifying a presence of the hydrogels to the predetermined depth with a non-invasive optical imaging technology.

16. The method of claim 15, wherein the hydrogels are polymeric and undergo biodegradation over a controllable time period.

17. The method of claim 15, wherein the hydrogels are water-containing polymers that are crosslinked.

18. The method of claim 15, wherein the hydrogels are covalent or non-covalent hydrogels.

19. The method of claim 15, wherein the non-invasive optical imaging technology includes optical coherence tomography (OCT) or fluorescence imaging.

\* \* \* \* \*